US006265193B1

(12) United States Patent
Brandis et al.

(10) Patent No.: US 6,265,193 B1
(45) Date of Patent: Jul. 24, 2001

(54) DNA POLYMERASES HAVING IMPROVED LABELED NUCLEOTIDE INCORPORATION PROPERTIES

(75) Inventors: John Brandis, Hercules; Curtis Bloom, Chino Hills; John H. Richards, Bradbury, all of CA (US)

(73) Assignees: PE Corporation (NY), Foster City; California Institute of Technology, Pasadena, both of CA (US)

( * ) Notice: Subject to any disclaimer, the term of this patent is extended or adjusted under 35 U.S.C. 154(b) by 0 days.

(21) Appl. No.: 09/041,878

(22) Filed: Mar. 12, 1998

Related U.S. Application Data (60) Provisional application No. 60/039,610, filed on Mar. 12, 1997.

(51) Int. Cl.[7] ..................................................... C12N 9/12
(52) U.S. Cl. ................................. 435/194; 435/6; 536/350
(58) Field of Search .......................... 435/6, 194; 536/350

(56) References Cited

U.S. PATENT DOCUMENTS

| | | | |
|---|---|---|---|
| 4,946,786 | * 8/1990 | Tabor et al. | 435/194 |
| 5,614,365 | * 3/1997 | Tabor et al. | 435/6 |
| 5,885,813 | * 3/1999 | Davis et al. | 435/183 |
| 5,939,292 | * 8/1999 | Gelfand et al. | 435/91.2 |
| 5,939,301 | * 8/1999 | Hughes, Jr. et al. | 435/194 |
| 5,945,312 | * 8/1999 | Goodman et al. | 435/91.1 |
| 5,948,614 | * 9/1999 | Chatterjee | 435/6 |

FOREIGN PATENT DOCUMENTS

| | | |
|---|---|---|
| 0727496 | 11/1994 | (EP) . |
| 0823479 | 7/1997 | (EP) . |

OTHER PUBLICATIONS

Kalman et al., "Thermostable DNA Polymerases with Altered Discrimination Properties," *Genome Sci. Technol* 1:42 (Abstract Only, A-14) (1995).

Reeve et al., "A novel thermostable polymerase for DNA Sequencing," *Nature* 376:796–797 (Aug. 31, 1995).

Suzuki et al., "Random mutagenesis of *Thermus aquaticus* DNA polymerase I:Concordance of immutable sites in vivo with the crystal structure," *Proc. Natl. Acad. Sci. USA* 93:9670–9675 (Sep., 1996).

Parker et al., "AmpliTaq DNA Polymerase, FS Dye–Terminator Sequencing: Analysis of Peak Height Patterns," *BioTechniques* 21(4):694–699 (Oct., 1996).

Voss et al., "Automated Cycle Sequencing with Taquenase: Protocols for Internal Labeling, Dye Primer and "Doublex" Simultaneous Sequencing," *BioTechniques* 23(2):312–318 (Aug., 1997).

* cited by examiner

*Primary Examiner*—Rebecca E. Prouty
*Assistant Examiner*—Richard Hutson
(74) *Attorney, Agent, or Firm*—Scott R. Bortner (57) ABSTRACT

The present invention relates to mutant DNA polymerases that exhibit reduced discrimination against labeled nucleotides into polynucleotides. The DNA polymerases of the invention have at least one mutation in the nucleotide label interaction region of the enzyme such the mutation results in reduced discrimination against labeled nucleotides. The nucleotide label interaction regions is located at portions of the O-helix, (ii) the K helix, and (iii) the inter O-P helical loop of Taq DNA polymerase or analogous positions in other DNA polymerases.

In addition to providing novel mutant DNA polymerases, the invention also provides polynucleotides encoding the subject mutant DNA polymerases. The polynucleotides provided may comprise expression vectors for the recombinant production of the mutant polymerases. The invention also provide host cells containing the subject polynucleotides. The invention also includes numerous methods of using the subject DNA polymerases, including uses for chain termination sequencing and PCR. Another aspect of the invention is to provide kits for synthesizing fluorescently labeled polynucleotides in accordance with the methods of the invention. Kits of the invention comprise a mutant DNA polymerase of the invention and a fluorescently labeled nucleotide that exhibits reduced discrimination with respect to the mutant DNA polymerase in the kit.

13 Claims, 4 Drawing Sheets

SEQUENCE LISTING

<160> NUMBER OF SEQ ID NOS: 4

<210> SEQ ID NO 1

```
<211> LENGTH: 25
<212> TYPE: DNA
<213> ORGANISM: Artificial Sequence
<220> FEATURE:
<223> OTHER INFORMATION: Irrelevant

<400> SEQUENCE: 1
ccctcgcagc cgtccaacca actca                                              25

<210> SEQ ID NO 2
<211> LENGTH: 36
<212> TYPE: DNA
<213> ORGANISM: Artificial Sequence
<220> FEATURE:
<223> OTHER INFORMATION: Irrelevant

<400> SEQUENCE: 2
gggagcgtcg gcaggttggt tgagtgcctc ttgttt                                  36

<210> SEQ ID NO 3
<211> LENGTH: 25
<212> TYPE: DNA
<213> ORGANISM: Artificial Sequence
<220> FEATURE:
<223> OTHER INFORMATION: Irrelevant

<400> SEQUENCE: 3
ccctcgcagc cgtccaacca actca                                              25

<210> SEQ ID NO 4
<211> LENGTH: 36
<212> TYPE: DNA
<213> ORGANISM: Artificial Sequence
<220> FEATURE:
<223> OTHER INFORMATION: Irrelevant

<400> SEQUENCE: 4
gggagcgtcg gcaggttggt tgagtaggtc ttgttt                                  36
```

DNA POLYMERASES HAVING IMPROVED LABELED NUCLEOTIDE INCORPORATION PROPERTIES

This application claims priority under 35 U.S.C. §119 (e) to provisional patent application Ser. No. 60/039,610 filed Mar. 12, 1997.

FIELD OF THE INVENTION

The invention is related to DNA polymerases having mutations that alter the ability of the enzyme to incorporate labeled nucleotides into a polynucleotide molecule.

BACKGROUND

DNA polymerases are enzymes that synthesize the formation of DNA molecules from deoxynucleotide triphosphates using a template DNA strand and a complementary synthesis primer annealed to a portion of the template. A detailed description of DNA polymerases and their enzymological characterization can be found in Kornberg, *DNA Replication Second Edition*, W. H. Freeman (1989).

DNA polymerases have a variety of uses in molecular biology techniques suitable for both research and clinical applications. Foremost among these techniques are DNA sequencing and nucleic acid amplification techniques such as PCR (polymerase chain reaction).

The amino acid sequence of many DNA polymerases have been determined. Sequence comparisons between different DNA polymerase have identified many regions of homology between the different enzymes. X-ray diffraction studies have determined the tertiary structures of Klenow fragment, T7 DNA polymerase, and Taq DNA polymerase. Studies of the tertiary structures of DNA polymerases and amino acid sequence comparisons have revealed numerous structural similarities between diverse DNA polymerases. In general, DNA polymerases have a large cleft that is thought to accommodate the binding of duplex DNA. This cleft is formed by two sets of helices, the first set is referred to as the "fingers" region and the second set of helices is referred to as the "thumb" region. The bottom of the cleft is formed by anti-parallel β sheets and is referred to as the "palm" region. Reviews of DNA polymerase structure can be found in Joyce and Steitz, *Ann. Rev. Biochem.* 63:777–822 (1994). Computer readable data files describing the three-dimensional structure of some DNA polymerases have been publicly disseminated.

Fluorescently labeled nucleotides have greatly simplified and improved the utility of many procedures in molecular biology. The use of fluorescently labeled nucleotides for labeling polynucleotides in synthesis procedures, has to a large extent replaced the use of radioactive labeling. Fluorescently labeled nucleotides have been widely used in DNA sequencing, see Smith et al Nature 321:674–679 (1986), in PCR, and other forms of polynucleotide fragment analysis.

A major problem with using fluorescently labeled nucleotides is the ability of DNA polymerases to discriminate against the incorporation of fluorescently labeled nucleotides. For example, the inventors have discovered that in competition assays between a TET (6-carboxy-4,7,2',7'-tetrachlorofluorescein) labeled 2'3' dideoxynucleotide and the corresponding unlabeled dideoxynucleotide, Taq DNA polymerase incorporates the unlabeled dideoxynucleotide into DNA at least 85 times more frequently than the corresponding unlabeled nucleotide. This discrimination between labeled and unlabeled nucleotides has profound effects on procedures using DNA polymerases to label DNA. For example, much larger amounts of fluorescently labeled nucleotide must be used in sequencing reactions. This large amount of fluorescently labeled nucleotide is expensive and can generate excessive background fluorescence, thereby reducing the yield of sequence information.

In view of the problems arising from the ability of DNA polymerases to discriminate against the incorporation of fluorescently labeled nucleotides, the inventors have developed several novel DNA polymerases that have reduced discrimination against the incorporation of one or more fluorescently labeled nucleotides into DNA.

SUMMARY

Naturally occurring DNA polymerases preferentially incorporate unlabeled nucleotides over corresponding fluorescently labeled nucleotides into polynucleotides. This ability of DNA polymerases to discriminate against fluorescently labeled nucleotide has undesirable effects on many molecular biology procedures that require the enzymatic addition of fluorescently labeled nucleotides, e.g., labeled dideoxy terminator sequencing. The present invention relates to mutant DNA polymerases that exhibit reduced discrimination against fluorescently labeled nucleotides into polynucleotides.

The DNA polymerases of the invention have at least one mutation in the nucleotide label interaction region of the enzyme such that the mutation results in reduced discrimination against fluorescently labeled nucleotides. The nucleotide label interaction region of a DNA polymerase is formed by portions of the O-helix, (ii) the K helix, and (iii) the inter O-P helical loop of Taq DNA polymerase or analogous positions in other DNA polymerases. Amino acid residues within the nucleotide label interaction region as defined by TET (II).ddC are E520. A531, L522, R523, E524, A525, H526, P527,I528, V529, E530, K531, I532, R536, E537, R573, Q582, N583, V586, R587, P589, Q592, R593, R595, D610, T612, Q613, E615, R636, D637, T640, F647, V654, D655, P656, L657, R659, R660, T664, E681, L682, A683, I684, P685, E688, F692, Q754, H784, L817, E820, L828, K831, and E832. The sites at R660, T664, and E681 are of prefered sites for introducing mutations. In a preferred embodiment of the invention for use with fluorescein-type dyes, a mutation is present at position 681 converting an E (glutamic acid) to M (methionine), i.e., E681M. In a preferred embodiment of the invention for use with fluorescein-fluorescein energy transfer dyes a mutation is present at position 657 converting an L (leucine) to a G (glycine). In addition to providing mutant Taq DNA polymerases having reduced discrimination against labeled nucleotides, the invention includes mutants derived from a wide variety of DNA polymerases, both thermostable and otherwise.

In addition to providing novel mutant DNA polymerases, the invention also provides polynucleotides encoding the subject mutant DNA polymerases. The polynucleotides provided may comprise expression vectors for the recombinant production of the mutant polymerases. The invention also includes host cells containing the subject polymerase polynucleotides.

The invention also includes numerous methods of using the subject DNA polymerases. The subject methods involve synthesizing a fluorescently labeled polynucleotide by means of a polynucleotide synthesis reaction catalyzed by a mutant DNA polymerase that has reduced discrimination against incorporating labeled nucleotides into polynucleotides. The subject methods of polynucleotide synthesis include the step of extending a primed polynucleotide template with at least one fluorescent labeled nucleotide, wherein the extension is catalyzed by a DNA polymerase that has reduced discrimination against labeled nucleotides into polynucleotides. The subject methods of synthesizing a fluorescently labeled polynucleotide may be used in a variety of methods such as Sanger sequencing and the polymerase chain reaction (PCR).

Another aspect of the invention is to provide kits for synthesizing fluorescently labeled polynucleotides in accordance with the methods of the invention. Kits of the invention comprise a mutant DNA polymerase of the invention and a fluorescently labeled nucleotide that exhibits reduced discrimination with respect to the mutant DNA polymerase in the kit.

DETAILED DESCRIPTION OF SPECIFIC EMBODIMENTS OF THE INVENTION

Terminology

Positions of amino acid residues within a DNA polymerase are indicated by either numbers or number/letter combinations. The numbering starts at the amino terminus residue. The letter is the single letter amino acid code for the amino acid residue at the indicated position in the naturally occurring enzyme from which the mutant is derived. Unless specifically indicated otherwise, an amino acid residue position designation should be construed as referring to the analogous position in all DNA polymerases, even though the single letter amino acid code specifically relates to the amino acid residue at the indicated position in Taq DNA polymerase.

Individual substitution mutations are indicated by the form of a letter/number/letter combination. The letters are the single letter code for amino acid residues. The numbers indicate the amino acid residue position of the mutation site. The numbering system starts at the amino terminus residue. The numbering of the residues in Taq DNA polymerase is as described in U.S. Pat. No. 5,079,352 (Gelfand). Amino acid sequence homology between different DNA polymerases permits corresponding positions to be assigned to amino acid residues for DNA polymerases other than Taq. Unless indicated otherwise, a given number refers to position in Taq DNA polymerase. The first letter, i.e., the letter to the left of the number, represents the amino acid residue at the indicated position in the non-mutant enzyme. The second letter represents the amino acid residue at the same position in the mutant enzyme. For example, the term "R660D" indicates that the arginine at position 660 has been replaced by an aspartic acid residue.

The term "discrimination" as used herein refers to the property of a DNA polymerase to preferentially incorporate unlabeled nucleotides over corresponding fluorescently labeled nucleotides into DNA, i.e., the DNA polymerase discriminates against the fluorescently labeled nucleotide. Preferential incorporation may be measured in an assay in which a fluorescently labeled 2'3' dideoxynucleotide and a corresponding unlabeled 2'3' dideoxynucleotide compete for incorporation into the same site of a polynucleotide. An example of such an assay can be found below in example 2.

The term "reduced discrimination" as used herein refers to reduction in discrimination against incorporation of a fluorescently labeled nucleotides in a mutant DNA polymerase as compared to the parent enzyme. A reduction in discrimination may be described quantitatively by reference to the selectivity assays in Example 2 or reference to other assays providing for measurement of the same properties of the polymerase. A reduction in selectivity number as measured by the selectivity assays is a reduction in discrimination and may be expressed by a ratio of selectivity numbers. For example, a mutant DNA polymerase with a selectivity number of 8 would have a 10-fold reduction in discrimination when compared with a parent DNA polymerase having a selectivity number of 80.

The term "parent" or "parent enzyme" is used to distinguish a mutant DNA polymerase from the DNA polymerase that the mutant enzyme was derived from. Thus any naturally occurring DNA polymerase may be referred to as parent enzyme. A first DNA polymerase having mutations with respect to a naturally occurring enzyme is also be referred to as a parent enzyme with respect to a second DNA polymerase having additional mutations.

The term "discrimination reducing mutations" refers to mutations in the nucleotide label interaction region of a DNA polymerase that result in reduced discrimination against the incorporation of fluorescently labeled nucleotides. The term is used to distinguish mutations in a DNA polymerase, including mutations in the nucleotide label interaction region, that do not reduce discrimination against fluorescently labeled nucleotides from mutations that do reduce discrimination.

The term "nucleotide" as used herein, unless specifically noted otherwise, is used broadly to refer to both naturally occurring nucleotide and a variety of analogs including 2',3' dideoxynucleotides.

The term "fluorescein-type dyes" refers to a class of xanthene dye molecules which include the following fused three-ring system:

where a wide variety of substitutions are possible at each deoxy ring position. A particularly preferred subset of fluorescein-type dyes include the 4,7,-dichorofluoresceins (Menchen). Examples of fluorescein-type dyes used as fluorescent labels in DNA sequencing methods include 6-carboxyfluorescein (6-FAM), 5-carboxyfluorescein (5-FAM), 6-carboxy-4,7,2',7'-tetrachlorofluorescein (TET), 6-carboxy-4,7,2',4',5',7'-hexachlorofluorescein (HEX), 5-(and 6)carboxy-4',5'-dichloro-2'7'-dimethoxyfluorescein (JOE), and 5-carboxy-2',4',5',7'-tetrachlorofluorescein (ZOE). Many times the designation -1 or -2 is placed after an abbreviation of a particular dye, e.g., HEX-1. The "-1" and "-2" (or "I" and "II") designations indicate the particular dye isomer being used. The 1 and 2 isomers are defined by the elution order (the 1 isomer being the first to elute) of free dye in a reverse-phase chromatographic separation system utilizing a C-8 column and an elution gradient of 15% acetonitrile/85% 0.1 M triethylammonium acetate to 35% acetonitrile/65% 0.1 M triethylammonium acetate.

The term "alkynylamino type linker" refers to an alkynylamino linker of the type as described in U.S. Pat. No. 5,047,519 (Hobbs), U.S. Pat. No. 5,151,507 (Hobbs), and U.S. patent application Ser. No. 08/696,808, filed Aug. 13, 1996. Additional alkynylamino type liners are described in U.S. patent application Ser. No. 08/833,855, filed Apr. 10, 1997.

Figure 4:
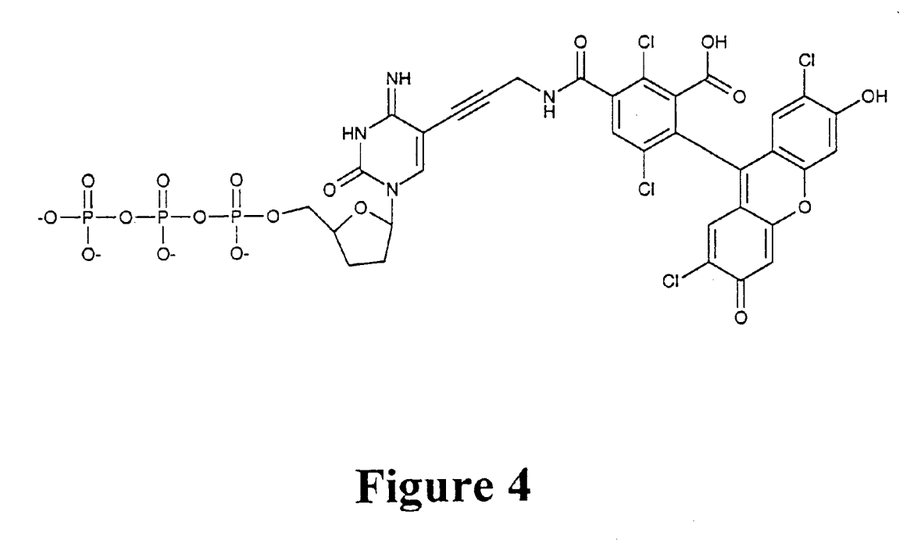
FIG. 4 is a representation of the structure of the fluorescently labeled nucleotide "TET(II).ddCTP."

The term "TET(II).ddCTP" refers to the fluorescently labeled nucleotide of the structure indicated in FIG. 4.

The term "fluorescence energy transfer dye" refers to dye moieties joined by a linker that permits fluorescence energy transfer between the two dye moieties. For use in chain termination sequencing, the linker is sufficiently small and of the proper shape and orientation to permit a DNA polymerase to incorporate a nucleotide triphosphate labeled with the dye interest. Examples of energy transfer dyes can be found in European Patent Application No. EP 0 805 140, U.S. patent application Ser. No. 08/642,330 (filed May 3, 1996), and U.S. patent application Ser. No.08/726,462 (filed Oct. 4, 1996).

The term "mutation" as used herein refers to a change in amino acid residue at a specific location of a protein. The change in amino acid residue is a change defined with respect to a naturally occurring protein. A protein having a mutation may be referred to as a "mutant" protein.

Embodiments of the Invention

The present invention relates to DNA polymerases containing mutations that reduce the ability of the polymerase to discriminate against the incorporation of fluorescently labeled nucleotides into polynucleotides. These mutations are in a region of the DNA polymerase molecule referred to herein as "the nucleotide label interaction region." The nucleotide label interaction region is formed by portions of three regions of the DNA polymerase. These three regions are located in (i) the O-helix, (ii) the K helix, and (iii) the inter O-P helical loop of Taq DNA polymerase or analogous positions in other DNA polymerases. DNA polymerases having reduced discrimination against fluorescently labeled nucleotides are particularly useful for chain termination DNA sequencing using 2'3' dideoxynucleotides, i.e., Sanger type sequencing.

Figure 1:
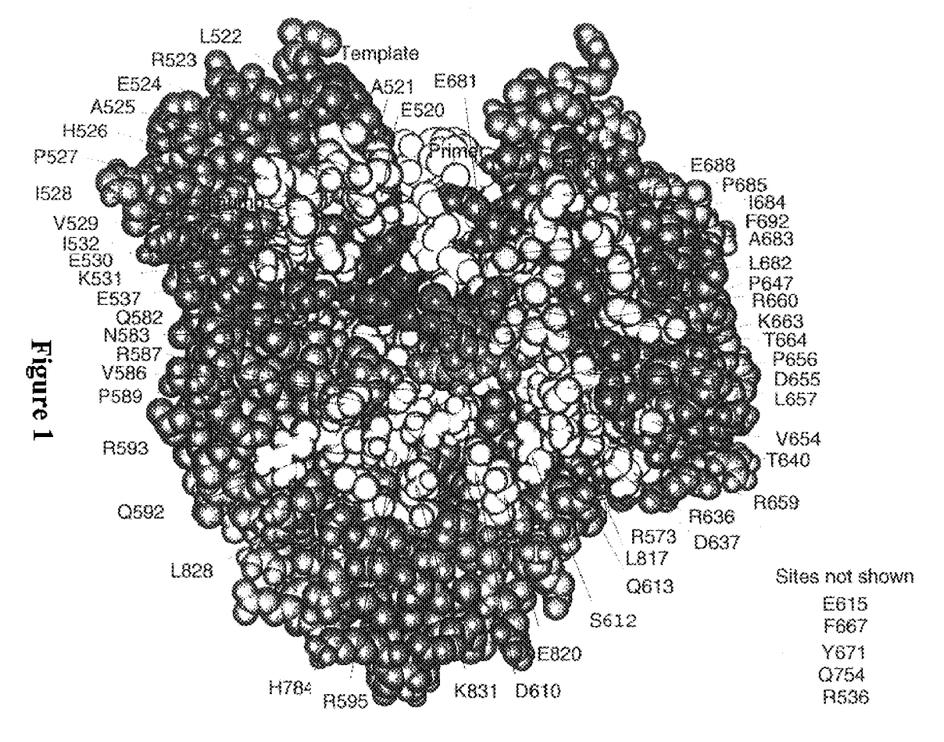
FIG. 1 is a computer model of DNA bound to Taq DNA polymerase. Amino acid residues that form the nucleotide label interaction site are highlighted in orange. The rest of the polymerase is indicated in green. The template is indicated in blue. The dye moiety of the labeled nucleotide is red. The remaider of the labled nucleotide is white.

Enzyme kinetic experiments (described in examples 2 and 3) performed with Taq DNA polymerase and fluorescently labeled dideoxynucleotides support a theory that Taq DNA polymerase and other DNA polymerases, undergo a conformational shift upon the binding of nucleotides during DNA synthesis. This predicted conformational shift suggests a set of amino acid residues that interact with fluorescent labels joined by a linker to the nucleic acid base of a nucleotide, thereby resulting in discrimination against nucleotides that are fluorescently labeled. This set of amino acid residues forms the nucleotide label interaction region. The specific molecular model for the binding of fluorescently labeled nucleotide to a DNA polymerase proposed by the applicants is used to predict the amino acid residues that form the nucleotide label interaction region of a given DNA polymerase. Applicants model for a conformational shift in DNA polymerase during DNA synthesis is offered as a explanation of how the nucleotide label interaction region was determined. The model provides guidance in making mutations in DNA polymerase that reduce the ability of a DNA polymerase to discriminate against the incorporation of fluorescently labeled nucleotides into polynucleotides. FIG. 1 is a computer model showing how DNA and Taq DNA polymerase interact in the model. Whether or not the true mechanism of DNA polymerase-nucleotide interaction is the same or different as the model used to determine the parameters of the nucleotide label interaction region is not determinative to the operability of the invention described herein.

The mutant DNA polymerases of the invention exhibit reduced discrimination against nucleotides labeled with a fluorescein-type dye. In other words, the mutant DNA polymerases of the invention contain at least one mutation that increases the ability of the polymerase to incorporate a fluorescein-type dye labeled nucleotide relative to the corresponding unlabeled nucleotide. In addition to reduced discrimination against nucleotides labeled with fluorescein-type dyes, the mutant DNA polymerases of the invention may also exhibit reduced discrimination against nucleotides labeled with other fluorescent dyes that are not fluorescein-type dyes, as well as reduced discrimination against other detectable moieties. The fluorescently labeled nucleotides for which a given embodiment of the mutant DNA polymerases of the invention exhibit reduced discrimination may vary with respect to the particular fluorescent label, the linker used to attach the fluorescent label to the nucleotide, the site of attachment for the linker on the fluorescent label, the specific nucleotide base that is selected, and the site of attachment for the linker on the nucleotide. The precise degree of reduction in discrimination against a fluorescently labeled nucleotide will vary in accordance with the specific mutation or mutations introduced into the DNA polymerase. The precise degree of reduction in discrimination will also vary in accordance with the specific fluorescently labeled nucleotide assayed, e.g., variations in base, dye, or linker. Mutant DNA polymerase of the invention may exhibit anywhere from a slight reduction in discrimination against fluorescently labeled nucleotides to a complete elimination in discrimination, i.e., the mutant enzyme does not significantly differ with respect of rate of incorporation of labeled or unlabeled nucleotides. It is preferable to use embodiments of the subject mutant DNA polymerases that have at least a two-fold reduction in discrimination against one or more fluorescein type dye labeled nucleotides.

It will be appreciated by persons skilled in the art of molecular biology that the nucleotide label interaction region of a given DNA polymerase is defined with respect to a specific fluorescently labeled nucleotide. Changes in one or more of the following parameters of the structure of a fluorescently labeled nucleotide may alter the identity of the amino acid residues that form the nucleotide label interaction site of a given DNA polymerase: (1) identity of the base, (2) the site of attachment on the nucleotide base, (3) the identity of the linker joining the base to the florescent dye, and (4) the identity of the fluorescent dye. The nucleotide labeled interaction region of Taq defined with respect to TET(II).ddCTP comprises the amino acid residues E520. A531, L522, R523, E524, A525, H526, P527, I528, V529, E530, K531, I532, R536, E537, R573, Q582, N583, V586, R587, P589, Q592, R593, R595, D610, T612, Q613, E615, R636, D637, T640, F647, V654, D655, P656, L657, R659, R660, T664, E681, L682, A683, I684, P685, E688, F692, Q754, H784, L817, E820, L828, K831, and E832. The sites at R660, T664, and E681 are of prefered sites for introducing mutations. Given that the 3-dimensional structure of Taq DNA polymerase (and other DNA polymerases) is well known and the three dimensional structure of TET(II) .ddCTP is understood with a high degree of certainty, the location of the amino acid residues that constitute the labeled nucleotide interaction region with respect to TET (II).ddCTP may be translated to a different set of amino acid residues to accommodate structural differences between TET(II).ddCTP and other fluorescently labeled nucleotides so as to define the labeled nucleotide interaction site with respect to those other nucleotides. For example, increasing the length of the linker between the base and the fluorescent label and the base may predictably alter the identity of amino acid residues that form the labeled nucleotide interaction site, even though the base, base attachment site, and fluorescent dye are the same. In many embodiments of the subject polymerases, the set of amino acid residues that form the labeled nucleotide interaction site with respect to a given fluorescently labeled nucleotide will overlap with the set of amino acid residues that form the labeled nucleotide interaction site as defined with respect to a second fluorescently labeled nucleotide.

Embodiments of the invention include mutant DNA polymerases that exhibit reduced discrimination against nucleotides labeled with fluorescein-type dyes, wherein the fluorescein type dye is joined to the nucleotide base by an alkynylamino-type linker. The fluorescein-type dye may be a fluorescent energy transfer dye, comprising a fluorescein-type dye moiety as a component of the energy transfer dye. In addition to reduced discrimination against fluorescently labeled nucleotides comprising an alkynylamino-type linker, the mutant DNA polymerases of the invention may also exhibit reduced discrimination against nucleotides comprising other types of linker. In order to minimize stearic interference between the polynucleotide and the fluorescent label, purines are usually labeled at position 7 and pyrimidines are usually labeled at position 5.

Mutant DNA polymerases of the invention have one or more discrimination reducing mutations at amino acid residue positions within the nucleotide label interaction region of a given DNA polymerase. Discrimination reducing mutations are usually, although not necessarily, substitution mutations. Several different amino residues may be substituted at a given position of a parent enzymes so as to give rise to a discrimination reducing mutations. The amino acid residues at a given residue position within the nucleotide label interaction region may be systematically varied so as to determine which amino acid substitutions result in the reduction of discrimination against the fluorescein-type dye labeled nucleotide dye of interest and the degree of such a reduction in discrimination. The extent to which a particular mutation (or set of mutations) reduces discrimination may be measured by a selectivity assay as described in example 2. The substitution mutation is preferably, although not necessarily, a mutation that reduces the size of the amino acid residue side chain of the amino acid residue present in the parent DNA polymerase. Mutations are preferably, although not necessarily, conservative so as to maintain the specific polar or non-polar character of the amino acid residue at the analogous position parent molecule. The mutations in the nucleotide label interaction region of a DNA polymerase preferably result in the substitution of the amino acid residue of the parent enzyme with the amino acid residue at the corresponding position of phage T7 DNA polymerase (provided that a difference exists between the amino acid residues at that position in T7 polymerase and the parent enzyme).

Discrimination reducing mutations are in the nucleotide label interaction region of DNA polymerases. The nucleotide label interaction region is formed by portions of three regions of the DNA polymerase. These three regions are located in (i)the O-helix, (ii) the K helix, and (iii) the inter O-P helical loop of Taq DNA polymerase or analogous positions in other DNA polymerases. Positions in Taq DNA polymerase that form the nucleotide label interaction region are positions E520. A531, L522, R523, E524, A525, H526, P527, I528, V529, E530, K531, I532, R536, E537, R573, Q582, N583, V586, R587, P589, Q592, R593, R595, D610, T612, Q613, E615, R636, D637, T640, F647, V654, D655, P656, L657, R659, R660, T664, E681, L682, A683, I684, P685, E688, F692, Q754, H784, L817, E820, L828, K831, and E832. Analogous positions in DNA polymerases other than Taq are also form a nucleotide label interaction region. Preferred positions for substitution mutations are R595, D655, R660, and E681. A particularly preferred position for mutations is E681, with the preferred substitution at position 681 being M. Other suitable substitution mutations at E681 are as follows (listed in order of decreasing preference, excpt where note by a equal sign to denote approximate equivalence"): M>I>W>L>V>P>H=K=G=T=S>D=A=N>Y=C. A preferred substitution mutation at position R660 is R660D.

The specific amino acid residues that form the nucleotide interaction region will vary in accordance with the particular DNA polymerase selected as a parent enzyme for the introduction of discrimination reducing mutations. The determination of analogous amino acid residues positions between different DNA polymerases may easily be achieved by the person skilled in the art because of the large number of DNA polymerase amino acid sequences that have been determined and the many regions of homology have been found between these different DNA polymerases. For example, a large compilation of the amino acid sequences of DNA polymerases from a wide range of organism and homology alignments between the sequences can be found in Braithwaite and Ito, *Nucl. Acids Res.* 21(4):787–802 (1993). Examples of amino acid residues within the nucleotide label interaction regions of phage T7 polymerase and *E. coli* DNA polymerase are provided in Table 1. In addition to providing mutant DNA polymerases having reduced discrimination for fluorescein type dyes in Taq, T7 and *E. coli* DNA polymerase I, the invention provides mutant DNA polymerases from many other organisms. In general, the teachings of the invention may used to produce mutant DNA polymerases having reduced discrimination for fluorescein type dyes from any DNA polymerase that shares sufficient amino acid sequence homology to Taq DNA polymerase to permit a person of ordinary skill in the art to identify one or more amino acid residue positions in the DNA polymerase that are analogous to positions E520. A531, L522, R523, E524, A525, H526, P527, I528, V529, E530, K531, I532, E537, R573, V586, R587, P589, Q592, R593, R595. D610, T612, Q613, E615, R636, T640, F647, V654, D655, P656, L657, R659, R660, T664, E681, L682, A683, I684, P685, E688, F692, Q754, L817, E820, L828, K831, and E832 in Taq DNA polymerase. Parent DNA polymerases that may be modified to contain discrimination reducing mutations in the nucleotide label interaction region include, but are not limited to, DNA polymerases from organisms such as *Thermus flavus, Pyrococcus furiosus, Thermotoga neapolitana, Thermococcus litoralis, Sulfolobus solfataricus, Thermatoga maritima, E. coli* phage T5, and *E. coli* phage T. The DNA polymerases may be thermostable or not thermostable. It will be appreciated that the present invention enables persons skilled in the art to introduce fluorescein-type dye discrimination reducing mutations in to DNA polymerases from a wide variety of organisms, including DNA polymerases that have not been isolated at the time of the filing of this application provided. Additionally, embodiments of the invention includes some purified naturally-occurring DNA polymerases that have the desired low degree of discrimination against fluorescently labeled nucleotides. Such naturally-occurring DNA polymerases are structurally and functionally analogous to the mutant DNA polymerases explicitly described herein.

The amino acid residues that constitute the nucleotide label interaction region of a given DNA polymerase vary in accordance with the specific fluorescently labeled nucleotide that is used to define the nucleotide label interaction region. Similarly, the mutations that are discrimination reducing mutations may vary in accordance with the specific fluorescently labeled nucleotide that is used to define the labeled nucleotide interaction region. Additionally, the degree of discrimination reduction achieved by the mutation (or mutations) in the labeled nucleotide interaction site may vary with the specific labeled nucleotide of interest. For example, E681M is the preferred discrimination reducing mutation in Taq with respect to TET(II).ddCTP resulting in a 47× reduction in discrimination and a significantly lower reduction in discrimination against a second fluorescently labeled nucleotide. Conversely, an E681T mutation may result in a high level reduction in discrimination against the second fluorescently labeled nucleotide and only a low level of reduction in discrimination against TET(II).ddCTP.

Given that a mutant DNA polymerase of the invention may have discrimination reducing mutation in the nucleotide label interaction region resulting in a significant degree of reduction in discrimination for a specific fluorescently labeled nucleotide and little or no reduction in the degree of reduction of discrimination against another fluorescently labeled nucleotide (assuming there is significant discrimination against that fluorescently labeled nucleotide by the parent DNA polymerase), a given mutant DNA polymerase may be said to be "receptive" with respect to one or more given fluorescently labeled nucleotide. A specific mutant DNA polymerase is referred to as "receptive" with respect to a specific fluorescently labeled nucleotide if a discrimination reducing mutation in the nucleotide label interaction site in the specific enzyme of interest results in at least a five fold reduction in discrimination against that given fluorescently labeled nucleotide. A mutant DNA polymerase of the invention may be receptive with respect to more than one fluorescently labeled nucleotide. Conversely, a specific fluorescently labeled nucleotide may be "receptive" with respect to a given mutant DNA polymerase of the invention.

In embodiments of the subject mutant DNA polymerases comprising more than one discrimination reducing mutation in the nucleotide label interaction region, the mutation site may be in the same or different region of the three regions of a polymerase that form the nucleotide label interaction region. In general, mutant DNA polymerases of the invention will have 1, 2, or 3 discrimination reducing mutations. However, the invention also provides mutant DNA polymerases having more than 3 discrimination reducing mutations. By combining multiple discrimination reducing mutations, greater levels of reduction in labeled nucleotide discrimination may be achieved. However, in many embodiments of the invention, mutant DNA polymerases have levels of reduced labeled nucleotide discrimination that are the same or less than the levels of DNA polymerase with single discrimination reduction mutations in the nucleotide label interaction region. Preferred combinations of mutations in a Taq DNA polymerase background are R660D, E681 G, and F667Y, i.e., Taq DNA polymerase mutant (R660D, E681G, and F667Y).

Different embodiments of DNA polymerase having mutations in the nucleotide label interaction region differ with respect to the degree of reduction in discrimination against specific fluorescently labeled nucleotides. These differences may be measured by an assay in order to determine which specific embodiments have the greatest degree of reduction in discrimination against the particular fluorescently labeled nucleotides of interest. Generally, such assays measure competition between a fluorescently labeled nucleotide and an unlabeled nucleotide for incorporation into the same site on a primed template. One example of such an assay (referred to herein as a "selectivity assay") is described in detail below in Example 2.

The mutant DNA polymerases of the invention may comprise numerous mutations in addition to discrimination reduction mutations in the nucleotide label interaction region. These secondary mutations may be either inside or outside the nucleotide label interaction region. Secondary mutations may be selected so as to have as to confer some useful property on the mutant DNA polymerase. For example, additional mutations may be introduced to increase thermostability; decrease thermostability, increase processivity, decrease processivity, decrease 3'–5' exonuclease activity, increase 3'–5' exonuclease activity, decrease 5'–3' exonuclease activity, increase 5'–3' exonuclease activity, and increase incorporation of dideoxynucleotides. Alternatively, the secondary mutations may be essentially neutral in known effect.

Of particular interest are embodiments of the subject mutant DNA polymerase that comprise one or more secondary mutation that reduce 3'–5' exonuclease activity. DNA polymerases that are deficient in 3'–5' exonuclease activity have superior properties for PCR and for chain termination polynucleotide sequencing. Mutations that reduce 3'–5' exonuclease activity in DNA polymerase are well known to person of ordinary skill in the art. Detailed guidance on how to introduce mutations that reduce 3'–5' exonuclease activity can be found, among other places in U.S. Pat. No. 4,795,699 (Tabor); U.S. Pat. No. 5,541,099; U.S. Pat. No. 5,489,523; and Bernad et al., *Cell* 59:219–288 (1989). Examples of such mutations in Taq DNA polymerase include G46D. For embodiments of the mutant DNA polymerases that are used for sequencing, it is preferable to include a G46D (or analogous mutations in DNA polymerases other than Taq) in addition to mutations in the nucleotide label interaction region.

Also of interest among secondary mutations in the subject DNA polymerase mutants are mutations that increase incorporation of dideoxynucleotides, i.e., reduce the ability of a DNA polymerase to discriminate against dideoxynucleotide as opposed to deoxynucleotides. Guidance on making such mutations can be found, among other places in published PCT application WO96/12042 (application number PCT/US95/12928). Of particular interest is the mutation F667Y in Taq and analogous mutations in other DNA polymerase. While F667Y is not part of the nucleotide label interaction region in Taq DNA polymerase with respect to Tet(II) .ddLTP, F667Y mutations may reduce discrimination against fluorescein-type dye labeled nucleotides (see Table 1). Accordingly, for use in certain procedures, e.g., DNA sequencing, be desirable to combine an F667Y mutations with one or more discrimination reducing mutations in the nucleotide label interaction region so as to reduce discrimination of the polymerase between deoxynucleotides and 2'3' dideoxynucleotides. Mutant DNA polymerase of the invention having the F667Y mutation (or equivalent thereof) are particularly useful in Sanger type DNA sequencing with fluorescently labeled 2'3' dideoxynucleotide chain terminators.

Numerous genes encoding DNA polymerases have been isolated and sequenced. This sequence information is available on publicly accessible DNA sequence databases such as GENBANK. A large compilation of the amino acid sequences of DNA polymerases from a wide range of organism can be found in Braithwaite and Ito, *Nucl. Acids Res.* 21(4):787–802 (1993). This information may be used in designing various embodiments of DNA polymerases of the invention and polynucleotide encoding these enzymes. The publicly available sequence information may also be used to clone genes encoding DNA polymerases through techniques such as genetic library screening with hybridization probes.

Other embodiments of the invention are polynucleotide sequences encoding the mutant DNA polymerases provided herein. Polynucleotide sequences encoding the mutant DNA polymerase of the invention may be used for the recombinant production of the mutant DNA polymerases. Polynucleotide sequences encoding mutant DNA polymerases having reduced discrimination against fluorescently labeled nucleotide may be produced by a variety of methods. A preferred method of producing polynucleotide sequences encoding mutant DNA polymerases having reduced discrimination against fluorescently labeled nucleotides is by using site-directed mutagenesis to introduce desired discrimination reducing mutations into polynucleotides encoding the parent DNA polymerase molecules. Site-directed mutagenesis techniques are well known in the art as exemplified by U.S. Pat. Nos. 4,711,848; 4,873,192; 5,071,743; 5,284,760; 5,354,670; 5,556,747; Zoller and Smith, *Nucleic Acids Res.* 10:6487–6500 (1982), and Edelman et al *DNA* 2:183 (1983). Detailed protocols for site-directed mutagenesis are also given many general molecular biology textbooks such as Sambrook et al Molecular Cloning a Laboratory Manual 2nd Ed. Cold Spring Harbor Press, Cold Spring Harbor (1989), Ausubel et al. Current Protocols in Molecular Biology, (current edition). Additionally, many text books on PCR (the polymerase chain reaction), such as Diefenbach and Dveksler, *PCR Primer: A Laboratory Manual,* Cold Spring Harbor Press, Cold Spring Harbor, N.Y. (1995), describe methods of using PCR to introduce directed mutations. Genes encoding parent DNA polymerase may be isolated using conventional cloning techniques in conjunction with publicly-available sequence information. Alternatively, many cloned polynucleotide sequences encoding DNA polymerases have been deposited with publicly-accessible collection sites, e.g., the American type culture collection deposit accession number ATCC 40336 is a phage clone of Taq DNA polymerase.

In addition to producing the mutant DNA polymerase encoding polynucleotides of the invention by introducing directed mutations into polynucleotides encoding parent DNA polymerases, it is possible (although difficult) to produce the polynucleotides of the invention primarily by in vitro DNA synthesis techniques. In vitro DNA synthesis techniques are well known to those skilled in the art and examples of in vitro DNA synthesis can be found in U.S. Pat. Nos. 5,252,530; 4,973,679; 5,153,319; 4,668,777; 4,500,707; 5,132,418; 4,415,732; 4,458,066; and 4,811,218. When producing relative polynucleotide molecules by in vitro DNA synthesis, smaller molecules are usually produced first and subsequently joined together by hybridization and ligation. Mutant DNA polymerase encoding polynucleotides may also be produced by a combination of in vitro synthesis and site-directed mutagenesis of cloned genes.

Polynucleotide encoding the mutant DNA polymerase of the invention may be used for the recombinant expression of the mutant DNA polymerases. Generally, the recombinant expression of the mutant DNA polymerase is effected by introducing a mutant DNA polymerase into an expression vector adapted for use in particular type of host cell. Thus, another aspect of the invention is to provide expression vectors comprising a polynucleotide encoding a mutant DNA polymerase of the invention, such that the polymerase encoding polynucleotide is functionally inserted int the expression vector. The invention also provide host cells comprising the expression vectors of the invention. Host cells for recombinant expression may be prokaryotic or eukaryotic. Example of host cells include bacterial cells, yeast cells, cultured insect cell lines, and cultured mammalian cells lines. Preferably, the recombinant host cell system is selected so as to closely match the organism from which the mutant DNA polymerase was derived. For example, prokaryotic DNA polymerases are preferably expressed in a prokaryotic expression system. A wide range of expression vectors are well known in the art. Description of various expression vectors and how to use them can be found among other places in U.S. Pat. Nos. 5,604,118; 5,583,023; 5,432,082; 5,266,490; 5,063,158; 4,966,841; 4,806,472; 4,801,537; and Goedel et al., *Gene Expression Technology, Methods of Enzymology,* Vol. 185, Academic Press, San Diego (1989). The expression of DNA polymerases in recombinant cell systems is a well-established technique. Examples of the recombinant expression of DNA polymerase can be found in U.S. Pat. Nos. 5,602,756; 5,545,552; 5,541,311; U.S. Statutory Inventor Registration H1,531; U.S. Pat. Nos. 5,500,363; 5,489,523; 5,455,170; 5,352,778; 5,322,785; and 4,935,361.

Other embodiments of the invention include multiple DNA polymerase compositions particularly useful for polynucleotide sequencing, such compositions comprise at least two different mutant DNA polymerases of the invention, wherein (1) the first mutant DNA polymerase is receptive with respect to a first fluorescently labeled nucleotide; (2) the second mutant DNA polymerase is receptive with respect to a second fluorescently labeled nucleotide; and (3) the first and second fluorescently labeled nucleotides differ from one another with respect to their nucleotide bases and fluorescent labels. The first and second fluorescently labeled bases may also differ with respect to one another by way of the linker, the base attachment position, or the fluorescent dye attachment site. The subject compositions are useful for catalyzing the sequencing reactions in Sanger type DNA sequencing with fluorescent dye labeled 2'3' dideoxy chain terminating nucleotides. Chain termination sequencing with fluorescently labeled terminators preferably employs at least two, and more preferably 4 different fluorescently labeled chain terminators, wherein each different base is labeled with a distinctive fluorescent label. Because of the necessary structural differences between the different fluorescently labeled chain terminators required for a sequencing reactions, i.e., nucleotide bases and fluorescent labels, there are many mutant DNA polymerases of the invention that are not receptive to all of the fluorescently labeled terminators necessary for a given sequencing reaction. Thus, there are embodiments of the subject DNA polymerases that may have undesirably high levels of discrimination against one or more of the labeled terminators used in a sequencing reaction set. The subject compositions of two or more mutant polymerases ameliorates this problem by simultaneously employing multiple mutant DNA polymerases that are receptive to different chain labeled terminators, thereby having at least one of the mutant polymerases "compensate" for the discrimination against a particular fluorescently labeled terminator by the other polymerases catalyzing the sequencing reactions. The ratio of the different DNA polymerases in the composition preferably are selected so as to result in approximately equal levels of total activity for each of the different mutant DNA polymerases. Differences in specific activity between the different mutant polymerases may be taken into account when equalizing total activity ratios between the polymerases. Differences in activity levels between the various mutant DNA polymerases in the subject compositions may also be compensated for by adjusting the levels of the different fluorescently labeled terminators in the subject compositions. The subject multiple polymerase compositions may comprise two, three, four, or more different mutant DNA polymerases. The mutant polymerase may or may not be derived from the same species or strain. The different mutation DNA polymerases in the subject mutant polymerase compositions may or may not be receptive for one or more of the fluorescently labeled nucleotides in a given set fluorescently labeled dideoxynucleotides for sequencing.

The invention also includes various methods of using the mutant DNA polymerases (or subject multiple mutant DNA polymerase compositions) of the invention. The mutant DNA polymerases of the invention may be substituted for the corresponding parent DNA polymerases in most procedures that employ DNA polymerases. In order to more fully take advantage of the properties of the subject mutant DNA polymerases, the amount (or concentration) of labeled and unlabeled nucleotides used in the methods of the invention may be changed with respect to the amounts (or concentrations) used in the corresponding methods employing convention DNA polymerases. These changes in the amount of nucleotide may be optimized by routine experimentation. Methods of the invention comprise the step of extending a primed polynucleotide template with at least one fluorescently labeled nucleotide, wherein the extension is catalyzed by a mutant DNA polymerase of the invention. Thus, the subject methods result in the formation of one or more different fluorescently labeled polynucleotides produced by primer extension. The subject methods of synthesizing a fluorescently labeled polynucleotide may be used in a variety of procedures including, but not limited to, Sanger sequencing (e.g., dideoxy nucleotide chain termination), the polymerase chain reaction (PCR), polynucleotide labeling, minisequencing. The reduced discrimination against fluorescently labeled nucleotide properties of the subject mutant DNA polymerase is particularly useful for Sanger DNA sequencing reactions, including cycle sequencing. The use of the subject mutant DNA polymerases for Sanger sequencing reduces the amount of fluorescently labeled chain terminating nucleotides required for a sequencing reaction an may in many case be used to increase the number of bases that may be identified in single sequencing reaction that is analyzed on an automated fluorescence-based sequencing apparatus such as an Applied Biosystems 310 or 377 (Applied Biosystems Division of Perkin-Elmer, Foster City, Calif.). Detailed protocols for Sanger sequencing are known to those skilled in the art and may be found, for example in Sambrook et al, Molecular Cloning, A Laboratory Manual, Second Edition, Cold Spring Harbor Press, Cold Spring Harbor, N.Y. (1989).

The invention also provides kits for synthesizing fluorescently labeled polynucleotides. The kits may be adapted for performing specific polynucleotide synthesis procedures such as DNA sequencing or PCR. Kits of the invention comprise a mutant DNA polymerase of the invention and a fluorescently labeled nucleotide that exhibits reduced discrimination with respect to the mutant DNA polymerase in the kit. Kits preferably contain detailed instructions on how to perform the procedures for which the kits are adapted. Optionally, the subject kit may further comprise at least one other reagent required for performing the method the kit is adapted to perform. Examples of such additional reagents include unlabeled nucleotides, buffers, cloning vectors, restriction endonucleases, sequencing primers, and amplification primers. The reagents include in the kits of the invention may be supplied in premeasured units so as to provide for greater precision and accuracy.

Other embodiments of the invention include kits comprising (1) the subject compositions of multiple mutant DNA polymerases, and (2) fluorescently labeled chain terminating nucleotides suitable for use with the subject compositions, i.e., each labeled chain terminator is receptive with respect to at least one of the mutant DNA polymerases in the composition. Additional embodiments of the invention include kits for sequencing DNA that comprise a multiple mutant polymerase composition of the invention and at least two different fluorescently labeled chain terminating nucleotides are labeled at different bases, wherein each of the fluorescently labeled chain terminating nucleotides is receptive with respect to at least one mutant DNA polymerase in the composition.

The invention, having been described above, may be better understood by reference to the following examples. The examples are offered, for among other reasons, to illustrate specific embodiment of the invention and should not be construed as a limitation on the invention.

EXAMPLES

Example 1

Purification of Mutant Forms of Taq DNA Polymerase

Lysates of *E. coli* containing recombinant constructs designed for the productiion of recombinant mutant Taq DNA polymerases were made essentially as described in tDesai, U. J. and Pfaffle, P. K., Biotechniques, 19:780–784 (1995). In order to prevent the polymerase from binding to chromosomal and plasmid DNAs contaminating the lysate, 5 M NaCl was added dropwise to the heat treated, clarified lysates to bring the final NaCl concentration to 0.25 M. DNA was then precipitated from this mixture by dropwise addition of 5% polyethylimine (in 20 mM TRIS.Cl, pH 8.5) to make the final concentration of PEI 0.3%. Precipitation was allowed to continue for 5 minutes on ice. A white, cloudy precipitate was removed by centrifugation at 15,000×g for 15 minutes at 4° C. The supernatant fluid was decanted and saved. Following centrifugation, the NaCl concentration was reduced to 0.13 M by monitoring conductivity of the solution during the addition of TETT minus NaCl (20 mM TRIS.Cl, 0.1 mM EDTA, 0.05% Tween-20, 0.05% Triton-X100, 1%. glycerol, pH 8.5).

Excess PEI was removed using a Bio-Rex 70 (BIO-RAD, Richmond, Calif.) column (2.5×30 cm). The column was poured and equilibrated with TETT Buffer+0.1 M NaCl. The polymerase does not bind to the Bio-Rex 70 under these conditions.

To remove contaminating *E. coli* proteins, the Bio-Rex 70 column eluate was loaded directly onto a Heparin-Agarose (Sigma Chemical Company, St. Louis, Mo.) column (1.5×30 cm) which was also poured and equilibrated in TETT Buffer+0.1 M NaCl. The heparin-agarose column was washed with 2 column volumes of TETT+0.1 M NaCl and Taq DNA polymerase was eluted as a sharp peak using TETT+1 M NaCl. Elution was monitored at 280 nm.

The heparin-agarose column fractions corresponding to the peak absorbance were pooled and concentrated to 0.15 ml using Ultrafree-15 Centrifugal Filter Devices (Millipore Corporation, Mass.) according to the manufacture's recommendations for centrifugation speeds and times. The concentrate was diluted to 15 ml with TETT Buffer+5% glycerol and the sample was re-concentrated to 0.15 ml. This was repeated one more time to reduce the final NaCl concentration below 1 mM in the protein samples.

The concentrated polymerase samples were diluted twofold using TETT+5% glycerol and an equal volume of TETT+95% glycerol was added to bring the final glycerol concentration to about 50%. Samples were stored at –20° C. Protein concentrations were determined using the "Bradford Protein Assay" (BIO-RAD, Richmond, Calif.). Activity was measured using a radiometric assay (described elsewhere).

Typical yields of polymerase from 2-liters of induced *E. coli* culture (corresponding to 30–50 ml of heat treated, clarified lysate) ranged from 4 to 24 mg. SDS-PAGE analysis of the purified samples showed one dark band of about 94,000 molecular weight) and several minor ones after Coomassie Blue staining. The gels indicated a typical purification level of >90%.

Example 2

Selectivity Assay

An unlabeled versus dye-labeled terminator assay ("terminator" is defined as a non-extendible base such as 2',3'-ddNTPs) was used to screen mutant Taq DNA polymerase samples for better Tet(II).ddCTP incorporating mutant forms of this polymerase. This assay is based upon two substrates competing for the same active site at the same time during a steady state reaction in which only the polymerase concentration is limiting. Therefore, the assay measure the polymerase's "selectivity" for the unlabeled versus the fluorescein-labeled terminator. The DNA Primer/template used in this assay format is given below:

5'→(FAM)-CCC TCG CAG CCG TCC AAC CAA CTC A (SEQ ID NO1).

GGG AGC GTC GGC AGG TTG GTT GAG T<u>G</u>C CTC TTG TTT←5' (SEQ ID NO:2).

The next template position following the 3'-end of the primer is indicated above by the bold and underlined G.

The reaction consisted of:
80 mM TRIS.Cl (pH 9.0 at 20° C.)
1000 nM DNA primer/template [5'-(FAM)25mer/36 G$_1$ template]
2 mM MgCl$_2$
50 μM TET(II).ddCTP
1 μM ddCTP
0.25 Units of enzyme
40 μL reaction volume
60° C. reaction temperature Samples (2 μL) were removed from the reaction mixture at pre-determined times (typically, 20 second intervals for 0.25 Units of polymerase activity per μL) and added to ice cold 50 μL 0.5 M EDTA (pH 8.0). Timed aliquots were mixed and held on ice for further processing.

Samples of each time point were processed to remove excess, unincorporated TET(II).ddCTP. Typically, 1.6 μL of each quenched sample were added to 250 μL of 0.8 M LiCl plus 0.2 μg/ml *E. coli* tRNA. followed by 750 μL of 95% ethanol. After mixing, the nucleic acids were allowed to precipitate for 20 minutes at –20° C. The precipitates were recovered by centrifugation using standard procedures. The supernatant fluid was discarded and pellets were dissolved in 50 μL of 50% formamide. Gel samples were heat treated (95° C. for 2 minutes) and 2 μL were loaded per sample lane on a 16% denaturing DNA sequencing gel. Gels were run on an Applied Biosystems Model 373 Sequencer using GeneScan Fragment Analysis software to measure the amount of FAM fluorescence in the bands corresponding to the 25-mer primer, the 26-mer product (indicating a ddC incorporation event) and the apparent "27-mer" product band (indicating a TET(II).ddC incorporation event).

The fluorescence signal in each of the bands was summed and the percent of signal in each band was used for further calculations as a normalization to avoid lane to lane loading differences. Energy transfer from the %-FAM moiety present on the apparent "27-mer" product molecules to the Tet(II) moiety on the newly incorporated 3'-base was not corrected since all ratios were compared to "wild type" or Taq G46D.) The normalized fluorescent signals in the 26-mer and "apparent" 27-mer product bands were corrected for the different concentrations of the two molecules used in the reaction and the corrected values were plotted versus time. The velocity of incorporation for each substrate was determined using least square fits to the data. The ratio of ddC/TET(II).ddC incorporation rates is equal to the selectivity bias that the sample polymerase shows for the unlabeled versus the TET(II)-labeled nucleotides and reflects the following relationship:

$$v_{ddC} \div v_{Tet.ddC} = (k_{cat}/K_M)_{ddC}[ddC] \div (k_{cat}/K_M)_{Tet.ddC}[Tet(II).ddC]$$

where:
$v_{ddC}$=velocity of ddC incorporation
$v_{Tet(II).ddC}$=velocity of Tet(II).ddC incorporation
$k_{cat}$=catalytic rate constant
$K_M$=necleotide equilibrium binding constant
[ddC]=concentration of ddCTP in the reaction
[Tet(II).ddC]=concentration of Tet(II)=YddCTP in the reaction In this assay format, "wild-type" Taq or (Taq G46D) showed a selectivity bias or ddC/Tet(II).ddC number of about 85 to 1. Mutants showing lower selectivity bias ratios were submitted to further testing. The Table 2 below shows the results for a few of the mutants tested by way of a few examples:

TABLE 2

| Taq | Selectivity Number | WT/Mutant |
|---|---|---|
| G46D | 85 | 85/85 or 1 |
| G46D; R660D | 8 | 85/8 or ≈10 |
| G46D; R595E | 28 | 85/28 or ≈3 |
| G46D; F667Y | 28 | 85/28 or ≈3 |
| G46D; E681G | 40 | 85/40 or ≈2 |
| G46D; D655L | 40 | 85/40 or ≈2 |

Example 3

Next Nucleotide Rate Effect Assay

An additional kinetic step between "ground state" nucleotide binding or initial collision and correct base pair formation and the group transfer reaction would be expected to slow the polymerase dissociation rate from an Enz.DNA complex having a 3'-dideoxynucleotide in an assay termed the "Next Nucleotide Rate Effect" (Patel et al., 1991). This assay measures the steady state rate of incorporation of ddTTP (i.e., the enzyme is limiting) in the absence or presence of the next correct nucleotide. The primer template pair is shown below:

5'→(FAM)-CCC TCG CAG CCG TCC AAC CAA CTC A (SEQ ID NO:3).

GGG AGC GTC GGC AGG TTG GTT GAG T<u>A</u>G GTC TTG TTT←5' (SEQ ID.NO:4)

The next template position is indicated by the bold, underlined A. The next template position beyond A is G.

Figure 2:
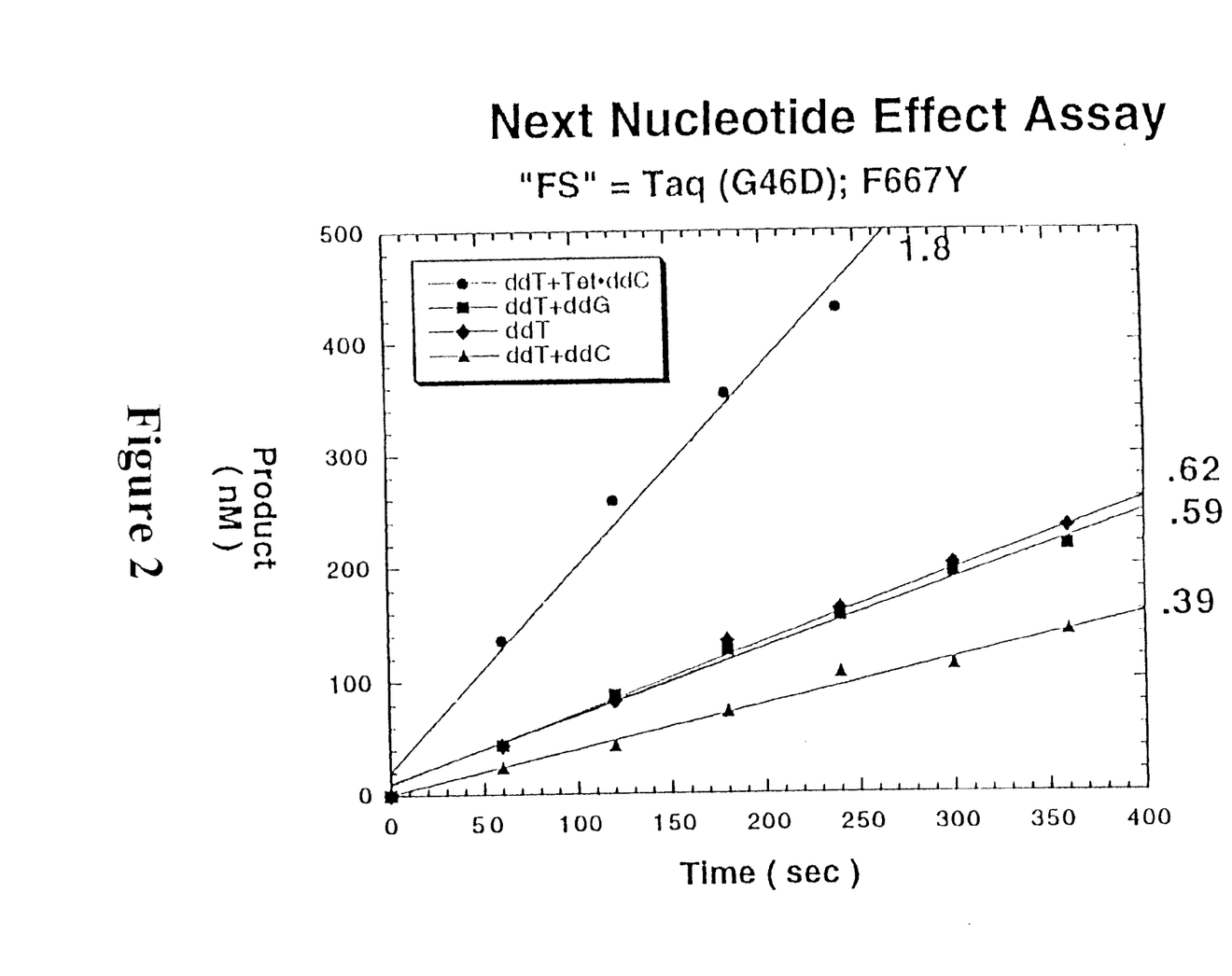
FIG. 2 is plot of a next nucleotide effect assay.

Under steady state reaction conditions, essentially all of the available polymerase is bound to the primer/template. When ddTTP is present alone in solution, it is incorporated following binding to its template position, A. Additional incorporation events require the polymerase to dissociate from the Enz.DNA complex and find another available primer/template that has not already undergone and incorporation event. Hence the rate of incorporation under these conditions is the dissociation rate of the polymerase from the Enz.DNA complex. If the next correct nucleotide, dGTP or ddCTP, is also present in the reaction mixture, the dissociation rate of the polymerase from the Enz.DNA.ddCTP complex, for example, will be slower if there is an additional kinetic step between the group transfer reaction that incorporated the ddTTP and an attempt by the polymerase to incorporate ddCTP in a processive mode of synthesis. This slower rate of dissociation an be detected as a slower incorporation rate of ddTTP since no chemistry can occur once ddTTP and the polymerase can no be processive despite the presence of another correct nucleotide. As shown in FIG. 2, the presence of the next correct nucleotide does indeed slow the turnover or dissociation rate of the polymerase (Taq G46D; F667Y). FIG. 2 also shows that the presence of a fluorescein dye on the next correct nucleotide (in this case, Tet(II).ddCTP), appears to accelerate the turnover rate. We interpret this to mean that the polymerase is constantly undergoing a conformational change and that it can attempt to undergo the change even in the absence of the next correct nucleotide. However, the presence of a fluorescein dye on the next correct nucleotide blocks the ability of the polymerase to undergo such a change and thereby causes an immediate dissociation of the enzyme following the group transfer step for ddTTP incorporation. Hence, the fluorescein dye appears to accelerate the polymerase dissociation rate by eliminating a kinetic step (or steps) following the group transfer reaction.

Figure 3:
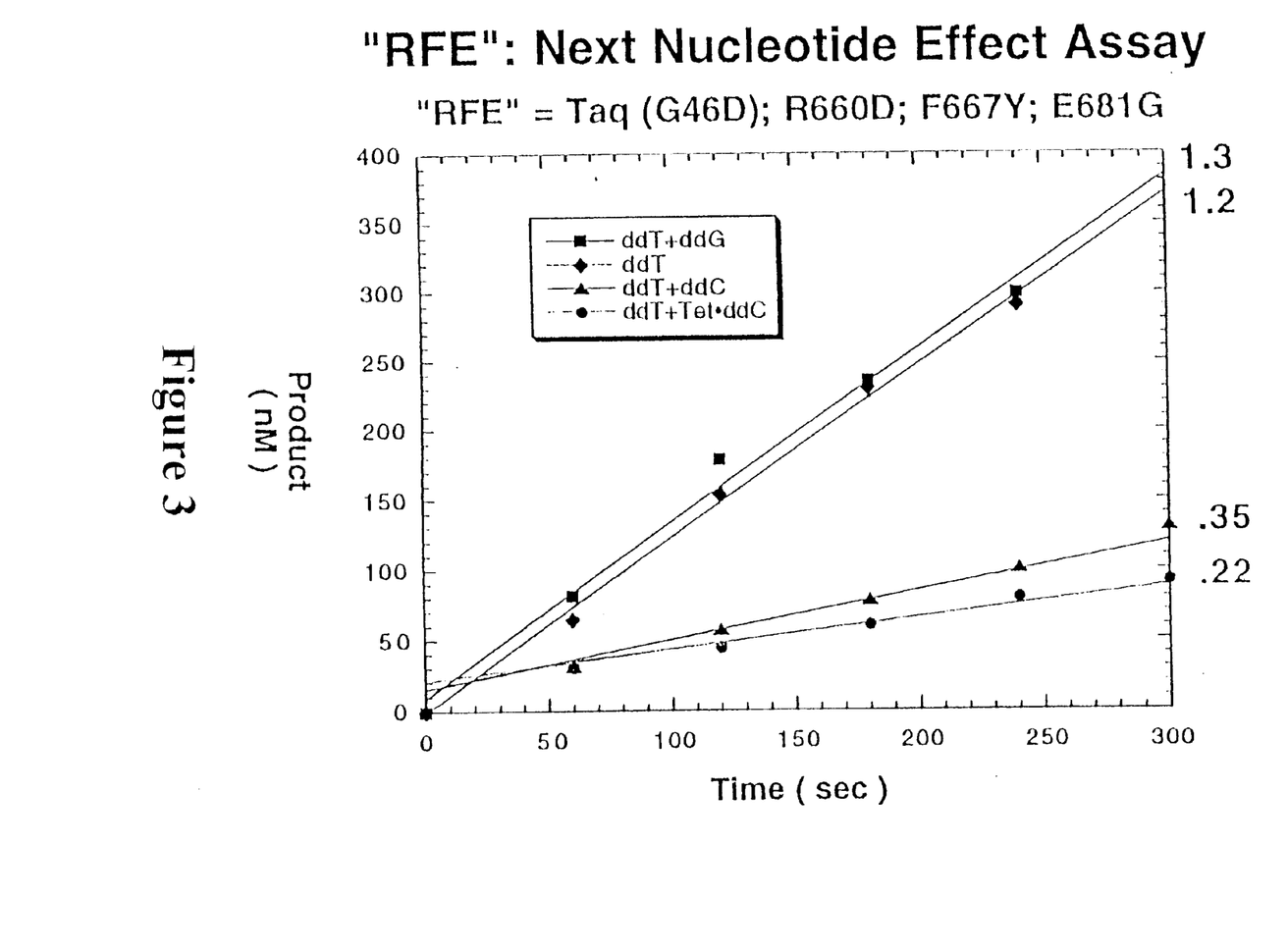
FIG. 3 is plot of a next nucleotide effect assay.

FIG. 3 shows the results for a Next Nucleotide Rate Effect assay for a "multiple" mutant form of Taq DNA polymerase, Taq G46D; R660D; F667Y; E681G. In this case, the presence of Tet(II) on the next correct nucleotide is "transparent" to the mutant polymerase. We interpret this to mean that the mutant polymerase can indeed undergo the same kinetic steps following group transfer that "wild-type" versions of this polymerase undergo. We also interpret these results to indicate that the F667Y mutation belongs in a different class than the R660D or E681G mutations since Taq G46D; F667Y still shows a "fluorescein-effect" in the "Next Nucleotide Rate Effect" assay, however, the multiple mutant, Taq G46D; R660D, F667Y; E681G, does not.

Typical assay conditions for the Next Nucleotide Effect assay were as follows:
1000 nM primer/template DNA
80 mM TRIS.Cl (pH 9.0 @20° C.)
2.4 mM $MgCl_2$
0.02 Units/$\mu$L polymerase activity
400 $\mu$M each nucleotide (when present)

Samples were taken and processed in the same manner as described under "Selectivity Assay." In this case, it is possible to distinguish a ddC-incorporation event from a Tet(II).ddC incorporation event by the migration rate of the resulting fragments in a 16% gel. Incorporation of ddC results in a "normal" 26-mer band that migrates as expected above or slower than the 25-mer primer. Incorporation of Tet(II).ddC results in slower migration causing the band to migrate with an apparent size equivalent to a 27- or 28-mer.

Example 4

Analysis of Additional Mutants

Table 1, provided below, provides a summary of results obtained with selectivity assays performed with several different Taq mutants. The analogous site for the mutation in the enzymes E. coli DNA polymerase I and phage T7 DNA polymerase are also noted. The term "FS" refers to a Taq DNA polymerase having a F667Y mutation.

References

Barnes, W. M. (1992) The fidelity of Taq polymerase catalyzing PCR is improved by an N-terminal deletion. *Gene* 112: 29–35.

Brandis, J. W., Edwards, S. G. and Johnson, K. A. (1996) Slow rate of phosphodiester bond formations accounts for the strong bias that Taq DNA polymerase shows against 2',3'-dideoxynucleotide terminators. *Biochemistry* 35: 2189–2200.

Desai, U. J. and Pfaffle, P. K. Single-step purification of a thermostable DNA polymerase expressed in *Escherichia coli*. *Biotechniques* 19: 780–784.

Fersht, A. (1985) in "Enzyme Structure and Function," W. H. Freeman and Company, 2nd ed., pp. 111–112.

Johnson, K. A. (1993) Conformational coupling in DNA polymerase fidelity. *Ann. Rev. Biochem.* 62: 685–713.

Patel, S. S., Wong, I., and Johnson, K. A. (1991) Pre-steady-state kinetic analysis of processive DNA replication including complete characterization of an exonuclease-deficient mutant. *Biochemistry* 30: 511–525.

Incorporation by Reference

This application incorporates all publications, patents, and patent application referenced herein in there entirety.

Equivalents

While the invention has been described and illustrated with reference to specific embodiments, those skilled in the art will recognize that modifications and variations may be made without departing from the principles of the invention as described hereinabove and set forth in the following claims.

TABLE 1

| No. | Taq Mutant | Pol I Equiv. | T7 Equiv. | [Final] $\mu$g/$\mu$l | "Units" per $\mu$l | Spec. Act. | TET(II)ddCTP/ ddCTP [Mut/Wt] | ROX.ddCTP/ ddCTP [Mut/Wt] | TAMRA.dTTP/ ddTTP [Mut/Wt] |
|---|---|---|---|---|---|---|---|---|---|
| 1 | G46D |  |  | 4.4 | 200 | 45.5 | 1* | 1 | 1 |
|  | G46D (LS.1) |  |  | 28.0 | 1950 | 69.6 |  |  |  |
|  | G46D (LS.2) |  |  | 78.3 | 6240 | 79.7 |  |  |  |
|  | FS |  |  | RMS |  |  | 3 |  | 920 |
| 2 | G46D; F667W | F762 | Y526 | 3.6 | 5 | 1.4 | 1 | 1 |  |
|  | (LS.1) | F762 | Y526 | 25.0 | 150 | 6.0 |  |  |  |
| 3 | G46D; R573E | R668 | R429 | 11.0 | 0 | 0.0 | nd | nd | nd |
| 4 | G46D; E615L | E710 | E480 | 4.8 | 0 | 0.0 | nd | nd | nd |
| 5 | G46D; E615D | E710 | E480 | 10.4 | 600 | 57.7 | no activity | nd | nd |

TABLE 1-continued

| No. | Taq Mutant | Pol I Equiv. | T7 Equiv. | [Final] μg/μl | "Units" per μl | Spec. Act. | TET(II)ddCTP/ ddCTP [Mut/Wt] | ROX.ddCTP/ ddCTP [Mut/Wt] | TAMRA.dTTP/ ddTTP [Mut/Wt] |
|---|---|---|---|---|---|---|---|---|---|
| 6 | G46D; E6151 | E710 | E480 | 7.0 | 140 | 20.0 | no activity | nd | nd |
| 7 | G46D; R587K | R682 | "V443" | 8.9 | 420 | 47.2 | 1 | 1 | 0.5 |
| 8 | G46D; R573K | R668 | R429 | 9.3 | 0 | | nd | nd | nd |
| 9 | G46D; L657T | E752 | T517 | 9.5 | 450 | 47.4 | 1 | 1 | |
| 10 | G46D; R587K | R682 | "V443" | nd | nd | nd | nd | nd | nd |
| 11 | G46D; Q754S | Q849 | Q615 | 13.0 | 0 | 0.0 | nd | nd | nd |
| 12 | G46D; E615K | E710 | E480 | 1.8 | 0 | 0.0 | nd | nd | nd |
| 13 | G46D; R573Q | R668 | R429 | 14.0 | 800 | 57.1 | 1 | 1 | |
| 14 | G46D; D655L | T750 | L515 | 11.3 | 400 | 35.4 | 2 | 0.7 | 0.5 |
| 15 | G46D; Q754K | Q849 | Q615 | nd | nd | nd | nd | nd | nd |
| 16 | G46D; R595K | R690 | H460 | nd | nd | nd | nd | nd | nd |
| 17 | G46D; K831M | H928 | H704 | 8.3 | 300 | 36.1 | 1 | 1 | |
| 18 | G46D; L682G | L777 | "I540" | 5.5 | 200 | 36.4 | 1 | 1 | 6 |
| 19 | G46D; R659K | R754 | D519 | 22.9 | 150 | 6.6 | no activity | nd | nd |
| 20 | G46D; A683E | N778 | V541 | 12.8 | 900 | 70.3 | 1 | | |
| 21 | G46D; Q754K | Q849 | Q615 | 5.0 | 0 | 0.0 | nd | nd | nd |
| 22 | G46D; R593H | R688 | E458 | 16.7 | 700 | 41.9 | 1 | | |
| 23 | G46D; R595E | R690 | H460 | 23.5 | 50 | 2.1 | 3 | | |
| 24 | G46D; A683V | N778 | V541 | 11.4 | 340 | 29.8 | 1 | | |
| 25 | G46D; Q592A | R687 | A457 | nd | nd | nd | nd | nd | nd |
| 26 | G46D; R660D | R755 | D519 | 13.3 | 190 | 14.3 | 10 | | |
| 27 | G46D; T640G | R735 | T507 | 13.0 | 225 | 17.3 | 1 | | |
| 28 | G46D; E681G | Q776 | "I540" | 7.5 | 170 | 22.7 | 2 | | |
| 29 | G46D; V654E | V749 | E514 | 9.2 | 210 | 22.8 | | | |
| 30 | G46D; Q613E | Q708 | G478 | 15.2 | 71 | 4.7 | | | |
| 31 | G46D; D610A | Q705 | D475 | 16.6 | 0 | 0.0 | nd | nd | nd |
| 32 | G46D; E820K | E917 | E693 | 11.6 | 475 | 40.9 | | | |
| 33 | G46D; L817A | L914 | L690 | 15.2 | 470 | 30.9 | | | |
| 34 | G46D; I684G | I779 | G542 | | | | | | |
| 35 | G46D; R660D; F667Y | | | 19.1 | 179 | 9.4 | 10 | | |
| 36 | G46D; R595E; R660D; F667Y | | | 10.5 | 0 | 0.0 | nd | nd | nd |
| 37 | G46D; D666L; R660D; F667Y | | | 18.8 | 228 | 12.1 | 10 | | |
| 38 | G46D; R660D; F667Y; E681G | | | 13.1 | 404 | 30.8 | 12 | | |
| 39 | G46D; R595E; F667Y | | | 9.5 | 0 | 0.0 | nd | nd | nd |
| 40 | G46D; T7 Loop JK | | | 12.7 | 0 | 0.0 | nd | nd | nd |
| 41 | G46D; A582Q583 | | | 13.2 | 0 | 0.0 | nd | nd | nd |
| 42 | G46D; P656S | S751 | P516 | 16.2 | 560 | 34.6 | | | |
| | G46D; R636A | K731 | G503 | | | | | | |
| | 40 Lysates | | | | 22 act. mutants | | 17 Tested 4 > "wt" | | |

*WT = 85

TABLE 2

| | Lysate #Genotype | | Specific Activity | Tet Selectivity TET(II)·ddCTP/ddCTP* (Mutant/WT) |
|---|---|---|---|---|
| R660- Mutants | | | | |
| Acidic | | | | |
| Aspartic Acid | 29 | CS; R660D | 14 | 10* |
| | 38 | FS; R660D | 9 | 10 |
| | 39 | R595E; FS; R660D | 0 | nd |
| | 40 | D655L; FS; R660D | 12 | 10 |
| | 41 | FS; R660D; E681G | 31 | 12 |
| | 49 | CS; R660D | 41 | nd |
| Glutamic Acid | 51 | FS; R660E; E681G | 11 | 7 |
| | 72 | FS; R660E | 1 | 7 |
| Basic | | | | |
| Lysine | 50 | FS; R660K | 28 | 1** |
| Histidine | 101 | FS; R660H | 13 | 1 |
| Imino- | | | | |
| Proline | 66 | FS; R660P | 8 | 1 |
| Aliphatic- | | | | |
| Alanine | 68 | FS; R660A | 4 | 4 |
| Isoleucine | 73 | FS; R660I | 5 | 0.9*** |
| Valine | 90 | FS; R660V | 10 | 1 |
| | 55 | FS; R660V; E681G | 1 | 1 |

TABLE 2-continued

| | Lysate # | Genotype | Specific Activity | Tet Selectivity TET(II)·ddCTP/ddCTP* (Mutant/WT) |
|---|---|---|---|---|
| Leucine | 91 | FS; G660L | 8 | 0.6*** |
| | 52 | FS; R660L; E681G | 28 | 1 |
| Glycine | 47 | FS; R660G; E681G | 18 | 6 |
| | 78 | FS; R660G | 8 | 2 |
| Polar Uncharged- | | | | |
| Glutamine | 53 | CS; R660Q | 47 | 1 |
| | 69 | FS; R660Q | 5 | 3 |
| Serine | 98 | FS; R660S | 16 | 7 |
| Cysteine | 93 | FS; R660C | 14 | 4 |
| Asparagine | 97 | FS; R660N | 13 | 3 |
| Threonine | 96 | FS; R660T | 26 | 3 |
| Methionine | | | | |
| Aromatic- | | | | |
| Phenylalanine | 92 | FS; R660F | 9 | 0.1*** |
| Tyrosine | 95 | FS; R660Y | 17 | 1 |
| E681- Mutants | | | | |
| Acidic- | | | | |
| Aspartic acid | 71 | FS; E681D | 9 | 4** |
| Basic- | | | | |
| Lysine | 75 | FSE681K | 52 | 6 |
| Arginine | | | | |
| Histidine | 86 | FS; E681H | 37 | 7 |
| Imino- | | | | |
| Proline | 74 | FS; E681P | 19 | 9 |
| Aliphatic- | | | | |
| Alinine | 63 | FS; E681A | 13 | 6 |
| Isoleucine | 99 | FS; E681I | 37 | 27 |
| Valine | 76 | FS; E681V | 110 | 10 |
| Leucine | 87 | FS; E681L | 22 | 14 |
| Glycine | 48 | FS; E681G | 37 | 6 |
| Polar Uncharged- | | | | |
| Glutamine | | | | |
| Serine | 61 | FS; E681S | 12 | 5 |
| Cysteine | 88 | FS; E681C | 20 | 2 |
| Asparagine | 89 | FS; E681N | 40 | 4 |
| Threonine | 81 | FS; E681T | 35 | 6 |
| Methionine | 85 | FS; E681M | 32 | 47 |
| Aromatic- | | | | |
| Phenylalanine | | | | |
| Tyrosine | 80 | FS; E681Y | 42 | 3 |
| Tryptophan | 84 | FS; E681W | 37 | 17 |

11-05-97
*Ratio > 1 means improved TET(II)·ddCTP incorporation.
enzyme.
**Ratio = 1 means wild-type activity.
***Ratio < 1 means activity worse than wild-type.
M > I > W > L > V > P > H=K=G=T=S > D=A=N > Y=C
47  27  17  14  10  9   7 6 6 6 5   4 4 4   3 2
Trytophan         94    FS; R660W         8         1

D > E=S > C=A=Q=T=N > G > K=P=V=Y=W=H >> I = L >> F
10  7 7   4 3 3 3     2   1 1 1 1 1      0.9  0.6    0.1
*Ratio > 1 means improved TET(II)·ddCTP incorporation. Must be "85" to be "transparent to the enzyme.
**Ratio = 1 means wild-type activity.
***Ratio < 1 means activity worse than wild-type

What is claimed is:

1. A purified DNA polymerase having at least one mutation as defined with respect to a naturally occurring DNA polymerase, wherein the mutation is at an amino acid residue position selected from the group consisting of E520, A531, L522, R523, E524, A525, H526, P527, I528, V529, E530, K531, I532, R536, E537, R573, Q582, N583, V586, R587, P589, Q592, R593, R595, D610, T612, Q613, R636, D637, T640, F647, V654, D655, P656, L657, R659, R660, T664, E681, L682, A683, I684, P685, E688, F692, Q754, H784, L817, E820, L828, K831, and E832, wherein the position of said amino acid residue within the DNA polymerase is defined with respect to Taq DNA polymerase and wherein the DNA polymerase has at least 2 fold reduced discrimination for a fluorescein-type dye labeled nucleotide as compared with the naturally occurring DNA polymerase.

2. A DNA polymerase according to claim 1, wherein the mutation is at a position selected from the group consisting of, R595, D655, R660, T664 and E681.

3. A DNA polymerase according to claim 2, wherein the mutation is selected from the group consisting of R660D, D655L, E681G, and R595E.

4. A DNA polymerase according to claim 3, comprising a mutation set belonging to the gorup consisting of (G46D, R660D, F667Y), (G46D, R595D, R660D, F667Y), and (G46D, R660D, F667Y, E681G), and (G46D,F667Y, E681G).

5. A DNA polymerase according to claim 1, wherein the DNA polymerase is a thermostable DNA polymerase.

6. A kit for fluorescently labeling a polynucleotide, the kit comprising a DNA polymerase according to claim 1 and a fluorescent dye labeled nucleotide.

7. A DNA polymerase according to claim 5, wherein the naturally occurring DNA polymerase is Taq DNA polymerase.

8. A kit according to claim 6, wherein the DNA polymerase is a thermostable polymerase.

9. A kit according to claim 8, wherein the naturally occurring DNA polymerase is Taq DNA polymerase.

10. A DNA polymerase according to claim 5, wherein the mutation is at a position selected from the group consisting of, R595, D655, R660, T664 and E681.

11. A DNA polymerase according to claim 10, wherein the DNA polymerase is Taq DNA polymerase.

12. A DNA polymerase according to claim 11, wherein the mutation is selected from the group consisting of R660D, D655L, E681G, and R595E.

13. A DNA polymerase according to claim 12, wherein said DNA comprises a mutation set belonging to the group consisting of (G46D, R660D, F667Y), (G46D, R595D, R660D, F667Y), and (G46D, R660D, F667Y, E681G), and (G46D, F667Y, E681G).

* * * * *